US012672852B2

(12) United States Patent
Bae et al.

(10) Patent No.: US 12,672,852 B2
(45) Date of Patent: Jul. 7, 2026

(54) METHOD AND DEVICE FOR EXTRACTING QUANTITATIVE INFORMATION IN MEDICAL ULTRASOUND

(71) Applicant: KOREA ADVANCED INSTITUTE OF SCIENCE AND TECHNOLOGY, Daejeon (KR)

(72) Inventors: Hyeon-Min Bae, Daejeon (KR); Myeong Gee Kim, Daejeon (KR); Seokhwan Oh, Daejeon (KR); Youngmin Kim, Daejeon (KR); Guil Jung, Daejeon (KR)

(73) Assignee: BARRELEYE INC, Daejeon (KR)

( * ) Notice: Subject to any disclaimer, the term of this patent is extended or adjusted under 35 U.S.C. 154(b) by 173 days.

(21) Appl. No.: 18/578,823

(22) PCT Filed: Jul. 1, 2022

(86) PCT No.: PCT/KR2022/009523
§ 371 (c)(1),
(2) Date: Jan. 23, 2025

(87) PCT Pub. No.: WO2023/287084
PCT Pub. Date: Jan. 19, 2023

(65) Prior Publication Data
US 2025/0359852 A1     Nov. 27, 2025

(30) Foreign Application Priority Data

Jul. 14, 2021     (KR) ........................ 10-2021-0091917
Mar. 17, 2022     (KR) ........................ 10-2022-0033572

(51) Int. Cl.
  *G16H 50/20*     (2018.01)
  *A61B 8/00*     (2006.01)
  (Continued)

(52) U.S. Cl.
  CPC .................. *A61B 8/48* (2013.01); *A61B 8/08* (2013.01); *A61B 8/463* (2013.01); *A61B 8/469* (2013.01);
  (Continued)

(58) Field of Classification Search
  CPC .. A61B 8/48; A61B 8/08; A61B 8/463; A61B 8/469; G06T 7/00; G06T 7/0012; G16H 30/40; G16H 50/20; G06N 3/08
  See application file for complete search history.

(56) References Cited

U.S. PATENT DOCUMENTS

2014/0364734 A1     12/2014   Huang
2017/0258438 A1 *   9/2017   Kanayama ............. A61B 8/085
(Continued)

FOREIGN PATENT DOCUMENTS

JP     2012-239546     12/2012
JP     2017-158917     9/2017
(Continued)

OTHER PUBLICATIONS

Nguyen TN, Podkowa AS, Park TH, Miller RJ, Do MN, Oelze ML. Use of a convolutional neural network and quantitative ultrasound for diagnosis of fatty liver. Ultrasound Med Biol. Mar. 2021;47(3):556-568. doi: 10.1016/j.ultrasmedbio.2020.10.025. Epub Dec. 25, 2020. PMID: 33358553; PMCID: PMC7828572. (Year: 2020).*
(Continued)

*Primary Examiner* — Boniface N Nganga
(74) *Attorney, Agent, or Firm* — LEX IP MEISTER, PLLC

(57) ABSTRACT

Disclosed is a method for extracting quantitative information by a device operated by at least one processor. The method includes: receiving pulse-echo data obtained from sensors of an ultrasound probe according to beam patterns radiated into a tissue; obtaining a location of a region of
(Continued)

interest (ROI); and extracting quantitative information on the ROI from the pulse-echo data by using a neural network trained to extract quantitative information from input data.

18 Claims, 14 Drawing Sheets

(51) Int. Cl.
| | | |
|---|---|---|
| *A61B 8/08* | (2006.01) | |
| *G06N 3/08* | (2023.01) | |
| *G06T 7/00* | (2017.01) | |
| *G16H 30/40* | (2018.01) | |

(52) U.S. Cl.
CPC ............. *G06N 3/08* (2013.01); *G06T 7/0012* (2013.01); *G16H 30/40* (2018.01); *G16H 50/20* (2018.01)

(56) References Cited

U.S. PATENT DOCUMENTS

| | | | |
|---|---|---|---|
| 2018/0185005 A1 | 7/2018 | Sandhu et al. | |
| 2019/0336108 A1* | 11/2019 | Hope Simpson ..... | G06T 7/0012 |
| 2021/0038195 A1* | 2/2021 | Li ........................ | A61B 8/4444 |

FOREIGN PATENT DOCUMENTS

| | | |
|---|---|---|
| JP | 6457157 | 1/2019 |
| JP | 2019-209130 | 12/2019 |
| JP | 2021-035442 | 3/2021 |
| JP | 2021-133123 | 9/2021 |
| KR | 10-2007-0069322 | 7/2007 |
| KR | 10-1121245 | 3/2012 |
| KR | 10-2013-0080640 | 7/2013 |
| KR | 10-2067340 | 1/2020 |
| KR | 10-2021-0075831 | 6/2021 |
| WO | 2020-254159 | 12/2020 |

OTHER PUBLICATIONS

Myeong-Gee Kim et al., "Robust Single-Probe Quantitative Ultrasonic Imaging System With a Target-Aware Deep Neural Network", IEEE transaction on Bio. vol. 68, No. 12, Jun. 7, 2021, total 2 pages (abstract only).

SeokHwan Oh et al., "A learned representation for multi-variable ultrasonic lesion quantification", 2021 IEEE 18th International Symposium on Biomedical Imaging (ISBI), Apr. 13-16, 2021, total 2 pages (abstract only).

SeokHwan Oh et al., "A neural framework for multi-variable lesion quantification through b-mode style transfer", Medical Image Computing and Computer Assisted Intervention—MICCAI 2021, Sep. 21, 2021, pp. 222-231.

Myeong-Gee Kim et al., "Quantitative imaging with a single probe in abdominal ultrasound", Proceedings vol. 12470, Medical Imaging 2023: Ultrasonic Imaging and Tomography, Apr. 10, 2023, total 1 page (abstract only).

Sanabria, Sergio J. et al., "Speed-of-Sound Imaging Based on Reflector Delineation", IEEE Transactions on Biomedical Engineering 66(7), Jul. 2019.

Cuiping Li et al., "In Vivo Breast Sound-Speed Imaging With Ultrasound Tomography", Ultrasound in Med. & Biol., vol. 35, No. 10, pp. 1615-1628, No. 10, 2009.

Myeong-Gee Kim et al., "Learning-Based Attenuation Quantification in Abdominal Ultrasound", M. de Bruijne et al. (Eds.): MICCAI 2021, LNCS 12907, pp. 14-23, 2021 (Sep. 21, 2021).

* cited by examiner

Encoding profile

FIG. 9

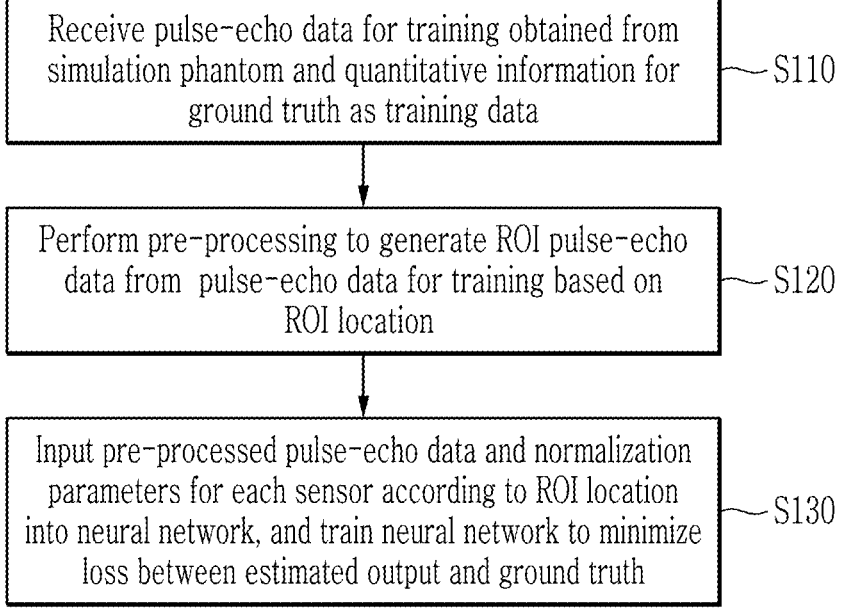

Receive pulse-echo data for training obtained from
simulation phantom and quantitative information for
ground truth as training data                          ~S110

Perform pre-processing to generate ROI pulse-echo
data from  pulse-echo data for training based on
ROI location                                           ~S120

Input pre-processed pulse-echo data and normalization
parameters for each sensor according to ROI location
into neural network, and train neural network to minimize
loss between estimated output and ground truth         ~S130

FIG. 11

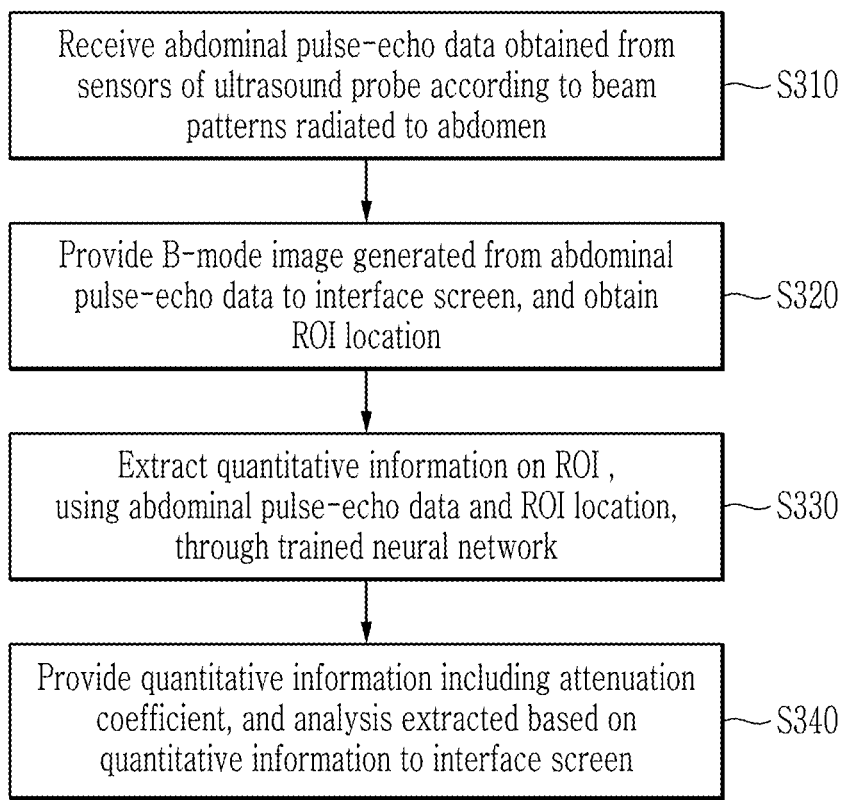

Receive abdominal pulse-echo data obtained from
sensors of ultrasound probe according to beam
patterns radiated to abdomen                              ～S310

Provide B-mode image generated from abdominal
pulse-echo data to interface screen, and obtain
ROI location                                             ～S320

Extract quantitative information on ROI ,
using abdominal pulse-echo data and ROI location,       ～S330
through trained neural network Provide quantitative information including attenuation
coefficient, and analysis extracted based on            ～S340
quantitative information to interface screen

FIG. 12

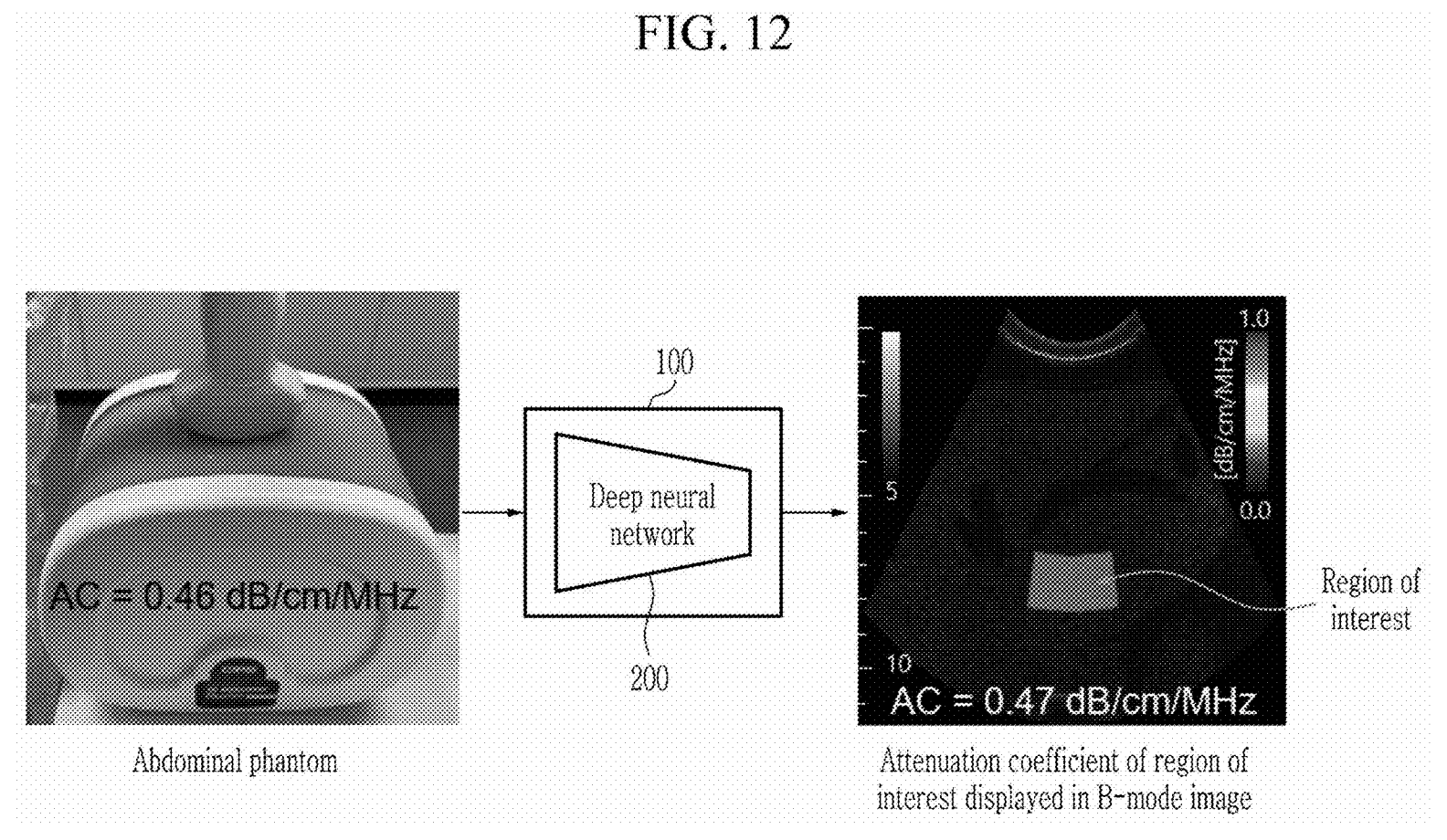

Abdominal phantom

AC = 0.46 dB/cm/MHz

Deep neural network

100

200

Region of interest

AC = 0.47 dB/cm/MHz

[dB/cm/MHz]

Attenuation coefficient of region of interest displayed in B-mode image

METHOD AND DEVICE FOR EXTRACTING QUANTITATIVE INFORMATION IN MEDICAL ULTRASOUND

TECHNICAL FIELD

The present disclosure relates to ultrasound quantification technology.

BACKGROUND ART

Hepatic steatosis is a common liver disease. Hepatic steatosis may be diagnosed through a biopsy, but this invasive method has the risk of infection and sampling errors. Magnetic Resonance Imaging (MRI) may noninvasively quantify hepatic steatosis, but its high cost and limited accessibility prevent its widespread use. Currently, medical ultrasound is used to diagnose hepatic steatosis.

The most common commercially available ultrasound imaging equipment today is the B-mode imaging system. A B-mode imaging method is a method of recognizing a location and a size of an object through the time and intensity of ultrasonic waves reflected and travelling back from a surface of the object. B-mode finds a location of lesions in real time, so that users may efficiently obtain the desired images while monitoring lesions in real time, and is safe, relatively inexpensive, and accessible. However, the B-mode has the disadvantage that the quality of the image does not remain constant depending on the user's skill level, and it is impossible to extract quantitative information.

The Attenuation Coefficient (AC) of a tissue has great potential as a quantitative biomarker due to its high sensitivity to pathological characteristics. In particular, the attenuation coefficient is emerging as a new biomarker for the diagnosis of hepatic steatosis, but most commercially available ultrasound imaging equipment are limited in their ability to provide this quantitative information.

DISCLOSURE

Technical Problem

The present disclosure attempts to provide a method and a device for extracting quantitative information on medical ultrasound.

The present disclosure also attempts to provide a method and a device for extracting quantitative information, such as an attenuation coefficient, from pulse-echo data acquired by a single ultrasound probe.

The present disclosure also attempts to provide a neural network performing ROI Adaptive Normalization (RAN) depending on a location of a region of interest.

The present disclosure also attempts to provide a method and a device for providing hepatic steatosis-related information based on an attenuation coefficient of a liver region extracted from an abdominal ultrasound.

Technical Solution

An exemplary embodiment of the present disclosure provides a method for extracting quantitative information by a device operated by at least one processor. The method includes: receiving pulse-echo data obtained from sensors of an ultrasound probe according to beam patterns radiated into a tissue; obtaining a region of interest (ROI); and extracting quantitative information on the ROI from the pulse-echo data by using a neural network trained to extract quantitative information from input data.

The obtaining the ROI may include obtaining a location of the ROI in a B-mode image generated from the pulse-echo data.

The method may further include: extracting pulse-echo data of the ROI from the pulse-echo data according to a location of the ROI; and inputting the pulse-echo data of the ROI into the neural network.

The neural network may normalize a feature of each sensor by using normalization parameters of each sensor extracted according to the location of the ROI.

The neural network may be configured to encode a quantitative feature included in the input pulse-echo data to generate an encoding profile, and extract quantitative information from the encoding profile while normalizing the feature of each sensor through a ROI adaptive normalization layer.

The quantitative information may be an attenuation coefficient.

The pulse-echo data may be abdominal ultrasound data, and the ROI may include a partial region of a liver.

The method may further include extracting information on hepatic steatosis in the ROI based on the attenuation coefficient extracted from the pulse-echo data.

Another exemplary embodiment of the present disclosure provides a method for extracting quantitative information by a device operated by at least one processor. The method include: receiving pulse-echo data obtained from sensors of an ultrasound probe according to beam patterns radiated to an abdomen; providing a B-mode image generated from the pulse-echo data to an interface screen, and obtaining a region of interest (ROI) from the interface screen; inputting the pulse-echo data and a location of the ROI to a neural network trained to extract quantitative information from input data, and extracting quantitative information on the ROI; and providing the quantitative information and/or analysis extracted based on the quantitative information to the interface screen.

The method may further include extracting information on hepatic steatosis in the ROI based on the quantitative information including an attenuation coefficient.

The location of the ROI may be represented as a vector representing a depth and a steering angle from the ultrasound probe.

The neural network may include an ROI adaptive normalization layer that normalizes a feature of each sensor by using normalization parameters of each sensor extracted based on the location of ROI.

The neural network may be configured to encode a quantitative feature included in the input pulse-echo data to generate an encoding profile, and extract an attenuation coefficient of the interest region from the encoding profile while normalizing the feature of each sensor through the ROI adaptive normalization layer.

Still exemplary embodiment of the present disclosure provides a method for extracting quantitative information by a device operated by at least one processor. The method includes: extracting pulse-echo data of a region of interest (ROI) from pulse-echo data obtained according to beam patterns from sensors of an ultrasound probe; encoding the pulse-echo data of the ROI for each channel corresponding to a steering angle of a beam pattern, and integrating outputs encoded for each channel to generate an encoding profile; normalizing a feature of each sensor included in the encoding profile by using normalization parameters of each sensor extracted based on a location of the ROI; and extracting quantitative information on the ROI from a feature normalized adaptively to the location of the ROI.

The location of the ROI may be represented as a vector representing a depth and a steering angle from the ultrasound probe.

The normalization parameters of each sensor may be parameters that scale and shift a feature of each sensor.

The extracting the quantitative information on the ROI may include extracting the quantitative information on the ROI by using a regression network trained to extract quantitative information included in the encoding profile through a sequential regression layer.

The quantitative information may be an attenuation coefficient.

The pulse-echo data may be abdominal ultrasound data, and the ROI may include a partial region of a liver.

The method may further include extracting information on hepatic steatosis in the region of interest based on the attenuation coefficient of the region of interest.

Advantageous Effects

According to the exemplary embodiment, it is possible to extract quantitative information by using the ultrasound probe and the imaging device for B-brightness mode imaging without change, and in particular, it is possible to obtain the attenuation coefficient that is a biomarker used to determine hepatic steatosis through ultrasound.

According to the exemplary embodiment, it is possible to increase estimation accuracy and noise resilience through the ROI adaptive beam focusing and envelope detection.

According to the exemplary embodiment, it is possible to accurately extract attenuation coefficients through region-of-interest adaptive normalization.

According to the exemplary embodiment, it is possible to provide clinical validity through the correlation between the extracted attenuation coefficient and Proton Density Fat Fraction (PDFF) acquired by using MRI.

DESCRIPTION OF THE DRAWINGS

FIG. 9 is a flowchart of a training method for a neural network according to an exemplary embodiment.

FIG. 11 is a flowchart of a quantitative information providing method based on abdominal ultrasound according to an exemplary embodiment.

FIGS. 12 and 13 are diagrams illustrating a result of extracting an attenuation coefficient by using a neural network according to an exemplary embodiment.

MODE FOR INVENTION

Figure 1:
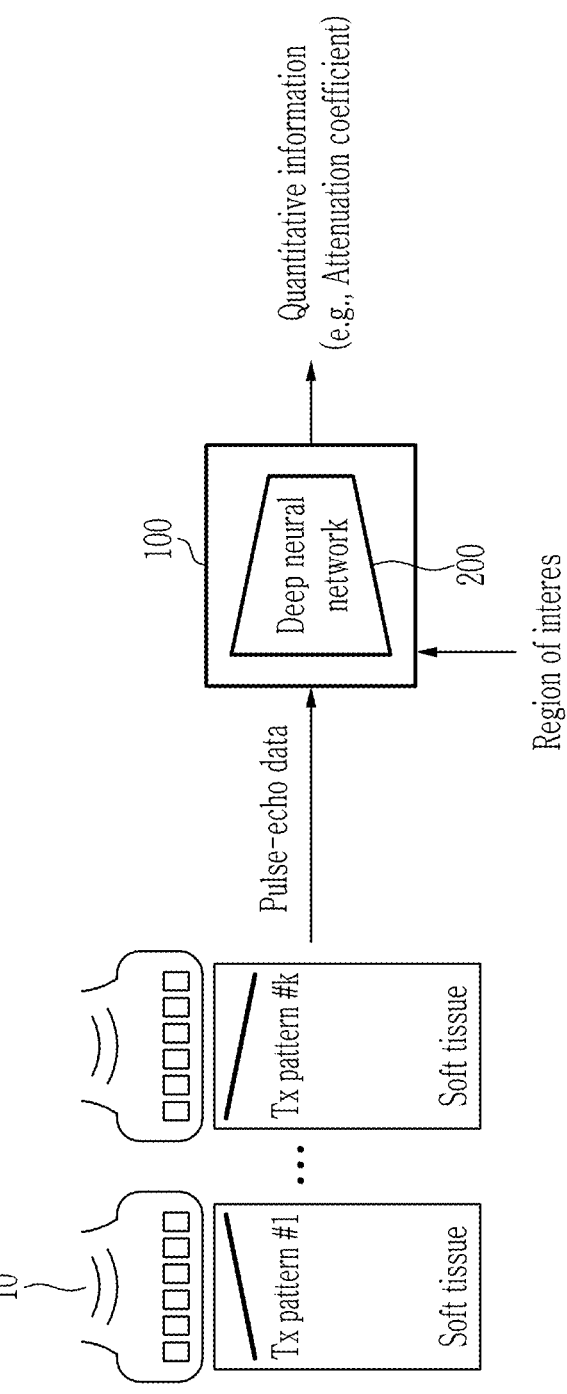
FIG. 1 is a conceptual diagram illustrating of a quantitative information extraction device according to an exemplary embodiment.

Hereinafter, exemplary embodiments of the present invention will be described with reference to accompanying drawings so as to be easily understood by a person ordinary skilled in the art. The present disclosure can be variously implemented and is not limited to the following exemplary embodiments. In addition, in order to clearly explain the present description in the drawings, parts irrelevant to the description are omitted, and similar parts are denoted by similar reference numerals throughout the specification.

Throughout the specification, unless explicitly described to the contrary, the word "comprise", and variations such as "comprises" or "comprising", will be understood to imply the inclusion of stated elements but not the exclusion of any other elements. In addition, the terms "-er", "-or", and "module" described in the specification mean units for processing at least one function and operation, and can be implemented by hardware components or software components, and combinations thereof.

The neural network of the present disclosure is an artificial intelligence model for learning at least one task, which may be implemented as software/program executed on a computing device. The program is stored on non-transitory storage media and includes instructions described to cause a processor to perform the operations of the present disclosure. Programs may be downloaded over a network or sold as a product.

Figure 2:
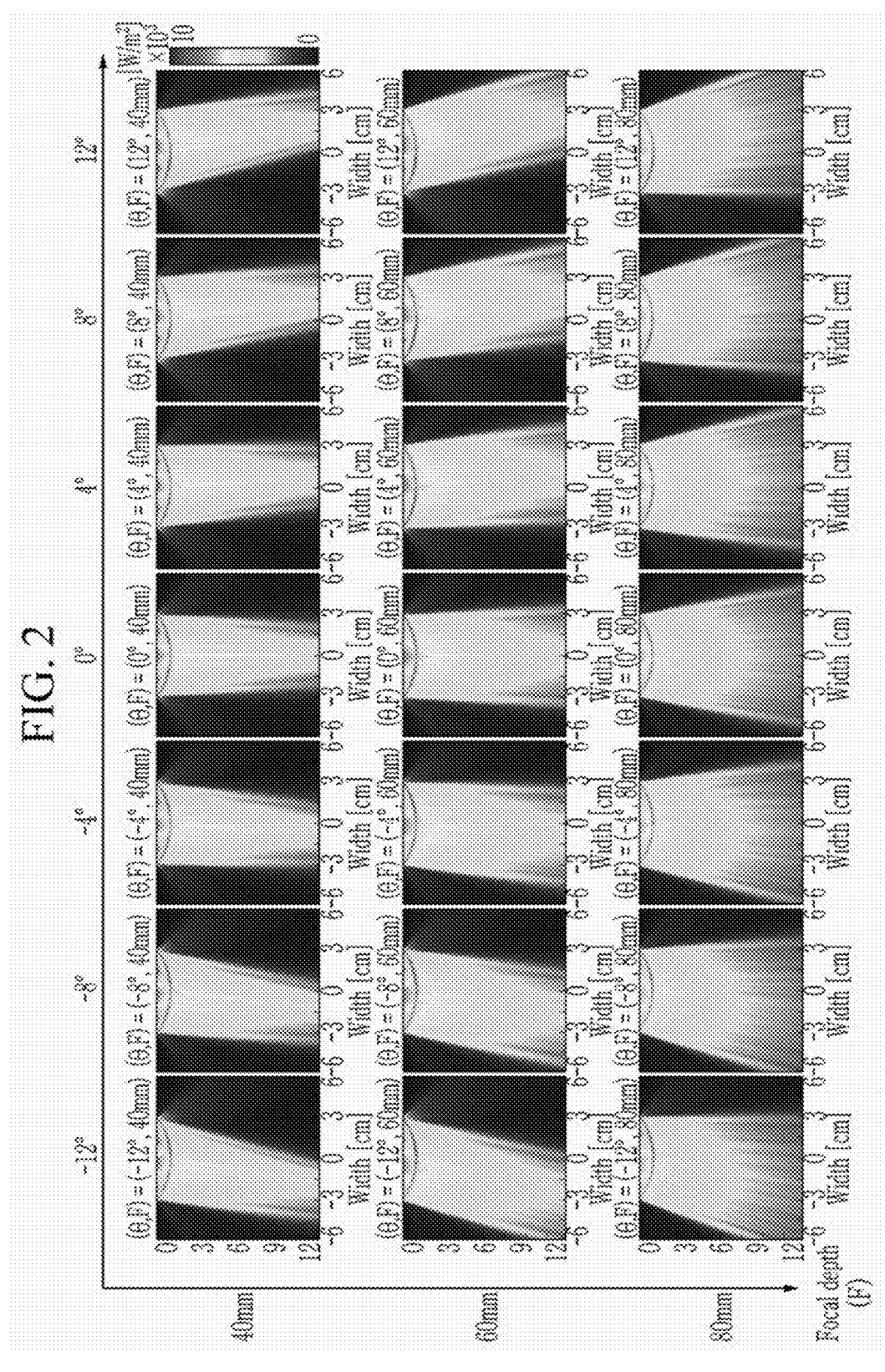
FIG. 2 is a diagram illustrating region-of-interest adaptive beam focusing.
Figure 3:
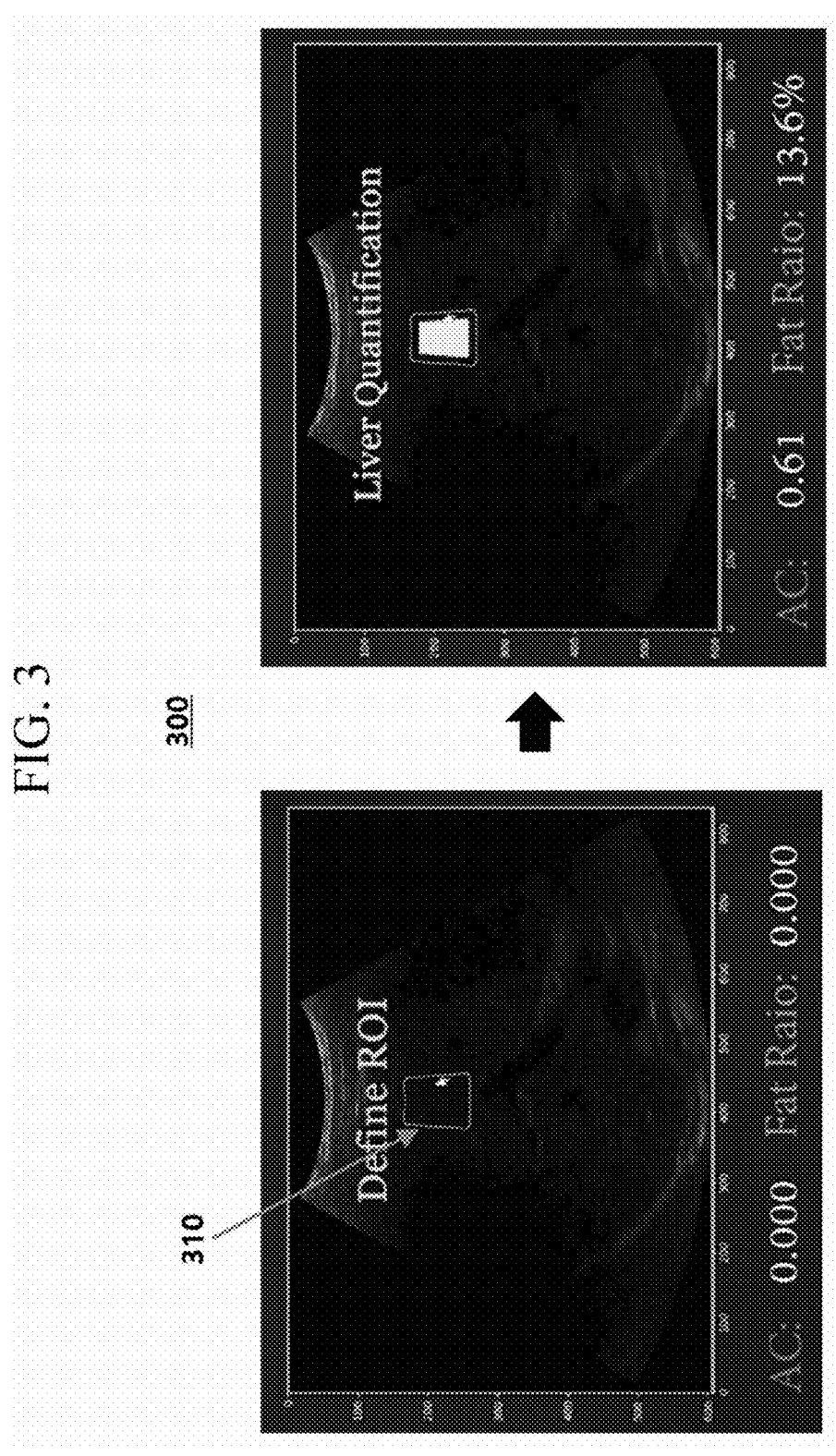
FIG. 3 is a diagram illustrating an example of a screen providing quantitative information on a region of interest according to an exemplary embodiment.
Figure 4:
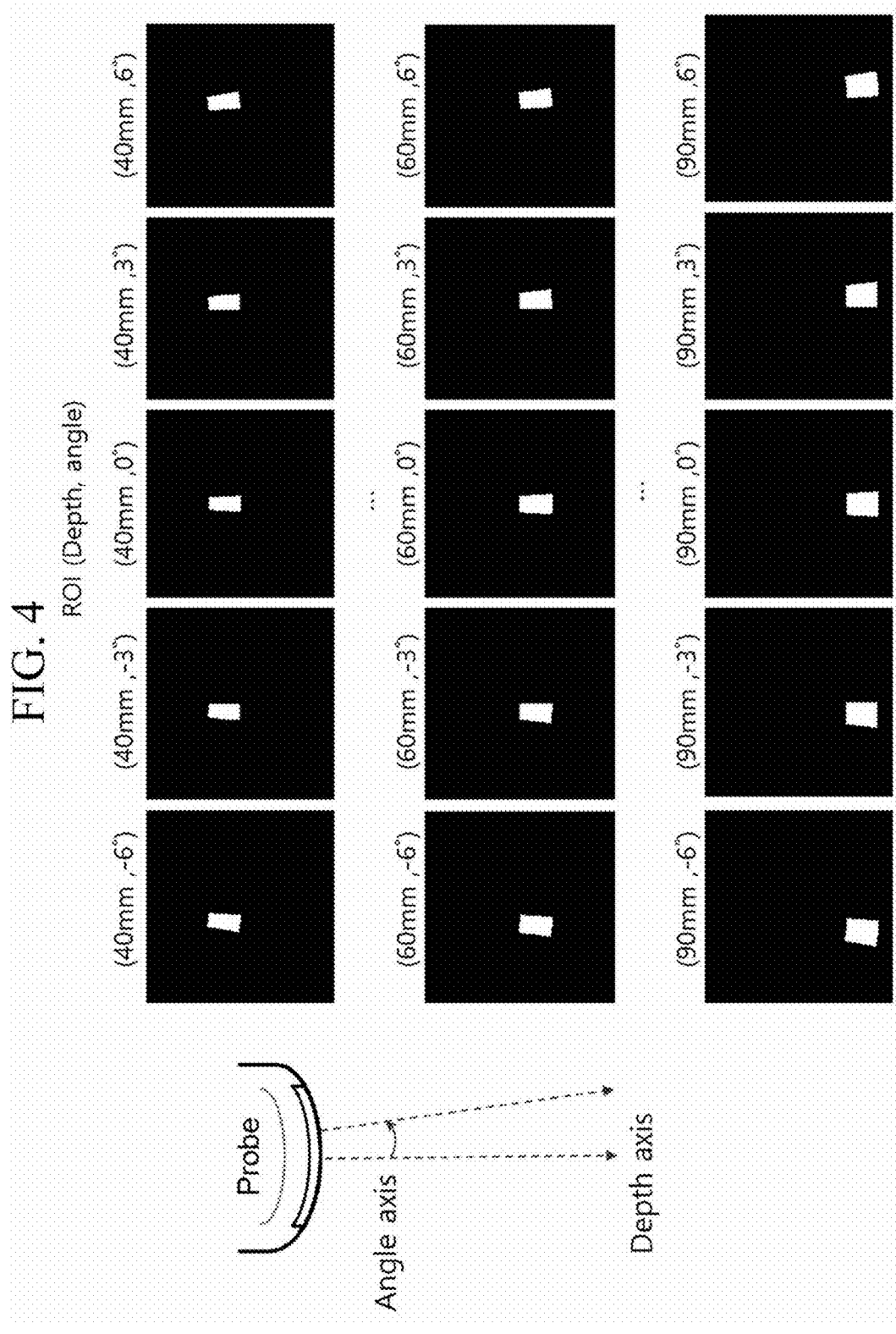
FIG. 4 is a diagram illustrating a location of a region of interest according to an exemplary embodiment.

FIG. 1 is a conceptual diagram illustrating of a quantitative information extraction device according to an exemplary embodiment, FIG. 2 is a diagram illustrating region-of-interest adaptive beam focusing, FIG. 3 is a diagram illustrating an example of a screen providing quantitative information on a region of interest according to an exemplary embodiment, and FIG. 4 is a diagram illustrating a location of a region of interest according to an exemplary embodiment.

Referring to FIG. 1, a quantitative information extraction device 100 is a computing device operated by at least one processor, and receives pulse-echo data obtained from a single ultrasound probe 10 as input and extracts quantitative information about a tissue by using a neural network 200. The quantitative information extraction device 100 is equipped with a computer program for the operations described in this disclosure, and the computer program is executed by a processor.

The quantitative information output by the neural network 200 may vary depending on training data, and is described herein by using an Attenuation Coefficient (AC) as an example. In addition, the neural network 200 may be trained to output quantitative information, such as sound speed, scatterer density, and scatterer size.

The ultrasound probe 10 may include an array of N (for example, 128) ultrasound sensors, and the sensors may be implemented as piezoelectric elements. Additionally, the ultrasound probe 10 may be a phased array probe that generates ultrasound signals by applying electrical signals to each element with time intervals. For reference, the ultrasound probe 10 may be a typical probe for B-mode imaging.

The ultrasound probe 10 may sequentially radiate ultrasound signals of different beam patterns (Tx pattern #1 to k) to the tissue and acquire radio frequency (RF) data reflected from the tissue and returned. RF data obtained from multiple beam patterns are collected and simply referred to as pulse-echo data. The pulse-echo data may be called beamformed ultrasound data. The beam pattern may be defined by a focal depth and a steering angle. For example, the ultrasound signal may be incident at seven steering angles (−12°, −8°, −4°, 0°, 4°, 8°, and 12°). The focal depth may be adjusted to, for example, six depths (40 mm, 50 mm, 60 mm, 70 mm, 80 mm, and 90 mm).

Meanwhile, the pulse-echo data obtained from the ultrasound probe 10 may include transmission time delay information for each sensor of the ultrasound probe 10. Pulse-echo data may be represented as an image with sensor-specific delay time information. The sensor-specific transmission time delay $D_T$ in the beam pattern (F,θ) may be calculated as shown in Equation 1.

$$D_T(Tx, \theta, F) = \frac{(\delta \cdot Tx)\sin\theta}{c_o} + \frac{\sqrt{F^2 + (\delta \cdot Tx)^2} - F}{c_o} \qquad \text{(Equation 1)}$$

In Equation 1, Tx is the order of the transmission sensors of the ultrasound probe 10, δ is the transducer spacing (pitch), $c_o$ is the average speed of sound, θ is the steering angle of the beam pattern, and F is the focal length of the beam pattern.

Referring to FIG. 2, the ultrasound probe 10 may focus the waves on the target area via region-of-interest (ROI) adaptive beam focusing. This allows to use the acquired pulse-echo data to improve estimation accuracy and noise resilience. For example, the ROI in an abdominal ultrasound may be a partial region of the liver.

The quantitative information extraction device 100 extracts quantitative information on the ROI from the pulse-echo data. The quantitative information extraction device 100 may receive the ROI from a user (operator) and extract quantitative information on the ROI from the pulse-echo data.

Referring to FIG. 3, the quantitative information extraction device 100 displays a B-mode image generated from the pulse-echo data on an interface screen 300, and receive a ROI 310 from the user (operator). The user may set at least one ROI on the interface screen 300. The location of the ROI 310 set on the interface screen 300 may be expressed by a depth from the ultrasound probe and an angle from the center axis of the ultrasound probe.

The quantitative information extraction device 100 may display quantitative information on the ROI 310, such as an Attenuation Coefficient (AC), on the interface screen 300. In addition, the quantitative information extraction device 100 may further display hepatic steatosis-related information, such as a fat ratio, extracted based on the quantitative information (e.g., attenuation coefficient) when the ROI 310 is a liver region.

Referring to FIG. 4, the location of the ROI 310 set on the interface screen 300 may be defined by, for example, a plurality of depth values (40 mm, 50 mm, 60 mm, 70 mm, 80 mm, and 90 mm) and a plurality of steering angle values (−6°, −3°, 0°, −3°, and 6°).

Alternatively, the location of the ROI 310, which is set on the interface screen 300, may be defined as a region of a certain size containing arbitrary coordinates selected by the user.

The quantitative information extraction device 100 may include a neural network 200 that adaptively normalizes the intensity of the pulse-echo data based on the location of the ROI, called ROI Adaptive Normalization (RAN). The quantitative information extraction device 100 may extract quantitative information (e.g., attenuation coefficients) from the pulse-echo data using the neural network 200. Since the attenuation of sound waves is a function of the attenuation characteristics of the transmission medium and the propagation distance, the quantitative information extraction device 100 adaptively normalizes the received data for each sensor based on the location of the ROI.

The quantitative information extraction device 100 may extract ROI data from the received pulse-echo data and input the extracted ROI data to the neural network 200. There are a variety of pre-processing methods to extract ROI data. For example, the quantitative information extraction device 100 may crop the pulse-echo data based on a ROI. In this case, the quantitative information extraction device 100 may perform envelope-detection for the pulse-echo data and crop the envelope-detected pulse-echo data based on the ROI. For example, when the pulse-echo data down to 15 cm is received, the quantitative information extraction device 100 may crop the pulse-echo data to obtain data of ROI, for example, a liver region in 6 cm depths.

The neural network 200 may extract quantitative information on the entire region from the pulse-echo data, and may extract quantitative information on the ROI from the quantitative information on the entire region. Alternatively, the neural network 200 may receive pulse-echo data that has been pre-processed with the data of the ROI to quickly and accurately extract quantitative information on the ROI. The neural network 200 may receive the envelope detected pulse-echo data. The neural network 200 may extract accurate quantitative information from the pulse-echo data regardless of the location of the ROI by using the ROI adaptive normalization method.

The neural network 200 includes an encoder to encode attenuation features contained in the pulse-echo data, and a decoder to reconstruct attenuation information from the output of the encoder. The decoder may be implemented in a variety of ways, and the following description uses a regression network as an example.

The neural network 200 may be configured to a sequential convolutional network for each channel corresponding to an angle in the beam pattern, and through the channel-specific sequential convolutional network, encode the attenuation features contained in the pulse-echo data which is input to the corresponding channel. In this case, the neural network 200 may receive cropped pulse-echo data based on the location of the ROI.

The neural network 200 trained to output attenuation coefficients may integrate the channel-specific encoded outputs to extract an encoding profile for the attenuation feature. The neural network 200 then extracts the attenuation coefficient contained in the encoding profile through a sequential regression layer. In this case, the neural network 200 may normalize the feature values of each sensor in the encoding profile by scaling and shifting the feature values of each sensor by using ROI-dependent parameters for each sensor of the ultrasound probe. To this end, the neural network 200 may include a ROI adaptive normalization (RAN) layer. Through the ROI adaptive normalization layer, the data acquired from the sensors is adjusted based on the location of the ROI to improve estimation accuracy and noise resilience.

Figure 5:
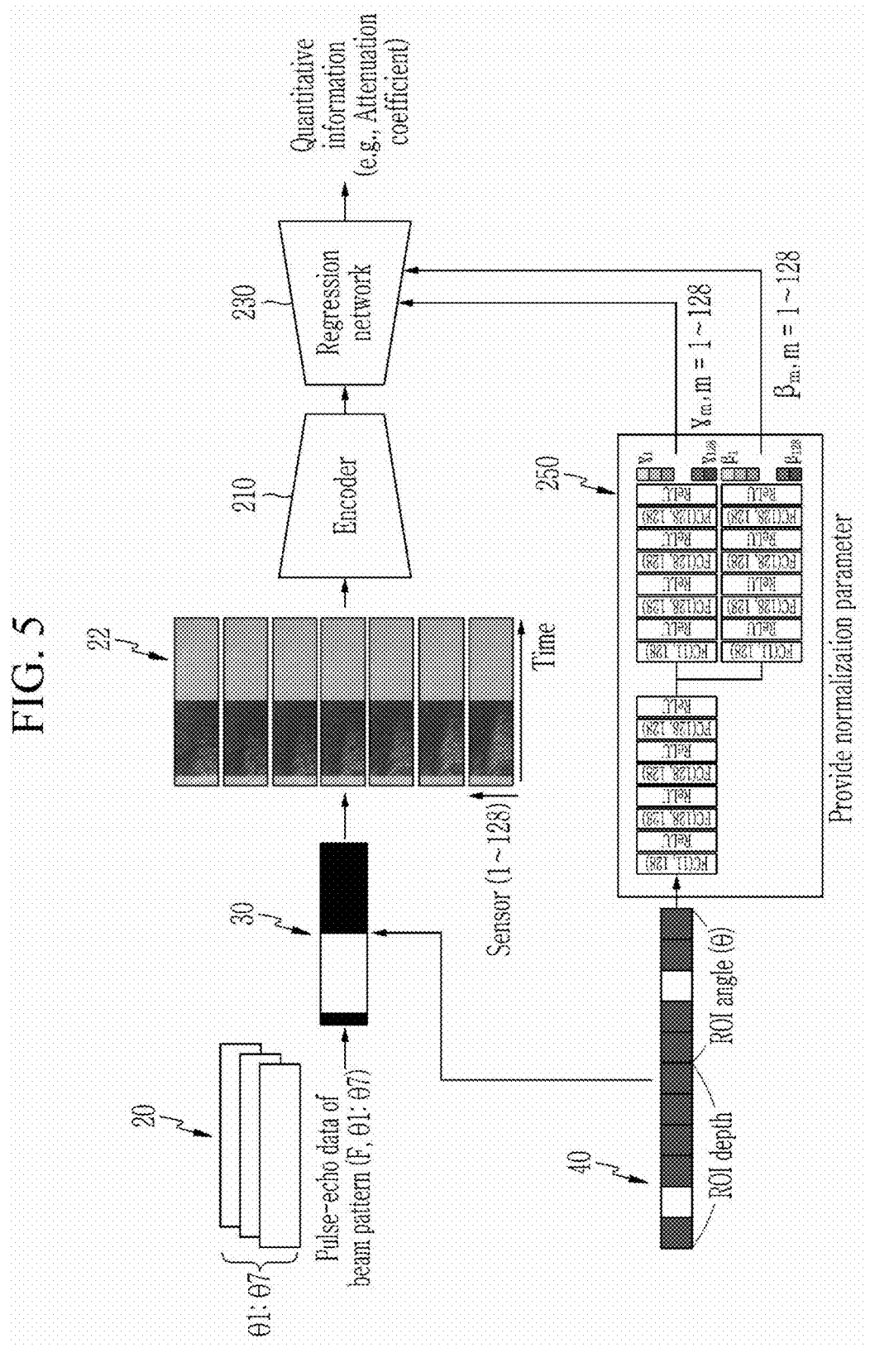
FIG. 5 is a conceptual diagram illustrating a neural network according to an exemplary embodiment.

FIG. 5 is a conceptual diagram illustrating the neural network according to an exemplary embodiment.

Referring to FIG. 5, the neural network 200 may include an encoder 210 that encodes quantitative features included in the pulse-echo data 20, and a regression network 230 that extracts quantitative information from the output of the encoder 210. Here, it is assumed that neural network 200 is trained to output an attenuation coefficient.

The pulse-echo data 20 is ultrasound data acquired by the ultrasound probe 10 for a beam pattern (F, θ1:θ7) of a particular focal depth (F) and steering angle (θ1:θ7). The pulse-echo data of each beam pattern may be acquired as an image of 128×2048 (number of sensors×time) size. The encoder 210 may receive input of pulse-echo data 20, but may also receive input of pulse-echo data 22 guided to a ROI. To this end, the quantitative information extraction device 100 may crop the pulse-echo data 20 based on the location of the ROI to generate the cropped pulse-echo data 22.

The quantitative information extraction device 100 may generate the pulse-echo data 22 of the ROI by pre-processing the pulse-echo data 20 according to the location of the ROI. For example, a crop mask 30 may be used to extract the pulse-echo data 22 of the ROI from the pulse-echo data 20. The crop mask 30 may be generated based on the location of the ROI. The location of the ROI may be represented by a ROI vector 40, which represents the depth and angle of the region of interest.

The ROI vector 40, which represents the location of the ROI, may be represented in various forms. For example, the ROI vector 40 may be represented as a combination of a one-hot vector representing the depth of the region of interest and a one-hot vector representing the steering angle. For example, the ROI vector 40 representing the location of the ROI may be an 11-dimensional vector representing six depths (40 mm, 50 mm, 60 mm, 70 mm, 80 mm, and 90 mm) and five steering angles (−6°, −3°, 0°, −3°, and 6°). For example, the ROI with a depth of 50 mm and an angle of 0° may be represented by "01000000100". When a user sets a ROI on the interface screen 300 of FIG. 4, the ROI vector 40 may be generated based on the location of the ROI.

The encoder 210 may receive the cropped pulse-echo data 22 as input, construct a sequential convolutional network for each channel corresponding to the beam pattern, and encode the attenuation feature contained in the pulse-echo data input to the corresponding channel through the channel-specific sequential convolutional network. The encoder 210 may integrate the encoded outputs for each channel to generate an encoding profile for the attenuation feature.

The regression network 230 may extract the attenuation coefficient contained in the encoding profile through sequential regression layer. In this case, the regression network 230 may normalize the feature of each sensor in the encoding profile by scaling and shifting the feature of each sensor, by using sensor-specific normalization parameters ($\gamma_m$, $\beta_m$) of the ultrasound probe. The sensor-specific normalization parameters may be ROI-dependent parameters. Since the attenuation of sound waves is a function of the attenuation characteristics of the transmitting medium and the propagation distance, the regression network 230 adaptively normalizes the received data based on the location of the ROI. For the sensor-level normalization, the regression network 230 may include a ROI adaptive normalization (RAN) layer.

The feature x(n, m) of each sensor may be normalized to X(n,m) by $\gamma_m$ and $\beta_m$, as shown in Equation 2. In Equation 2, n is the time, m is the sensor order, $\mu_m$ is the mean of the $m^{th}$ sensor's data, and $\sigma_m$ is the standard deviation of the $m^{th}$ sensor's data.

$$X(n, m) = \gamma_m \times \frac{x(n, m) - \mu_m}{\sigma_m} + \beta_m \qquad \text{(Equation 2)}$$

The sensor-specific normalization parameters $\gamma_m$, $\beta_m$ may be provided by a normalization parameter provider 250. The normalization parameter provider 250 may output parameters to normalize the feature of each sensor based on the location of the ROI. The location of the ROI may be represented by the ROI vector 40. The normalization parameter provider 250 may provide parameters to normalize the feature obtained from each sensor based on the location of the region of interest, for example, scaling parameters $\gamma_1$ to $\gamma_{128}$ and shifting parameters $\beta_1$ to $\beta_{128}$ for 128 sensors. The normalization parameters are ROI-dependent parameters, as they are generated based on the location of the ROI.

The normalization parameter provider 250 may have a variety of network structures that may receive the ROI vector 40 representing the location of the ROI and output sensor-specific normalization parameters. For example, the normalization parameter provider 250 may include four common blocks and four scaling parameter blocks and four shifting parameter blocks connected in parallel to the four common blocks. Each block may consist of a fully-connected layer and an active layer (e.g., ReLU).

Figure 6:
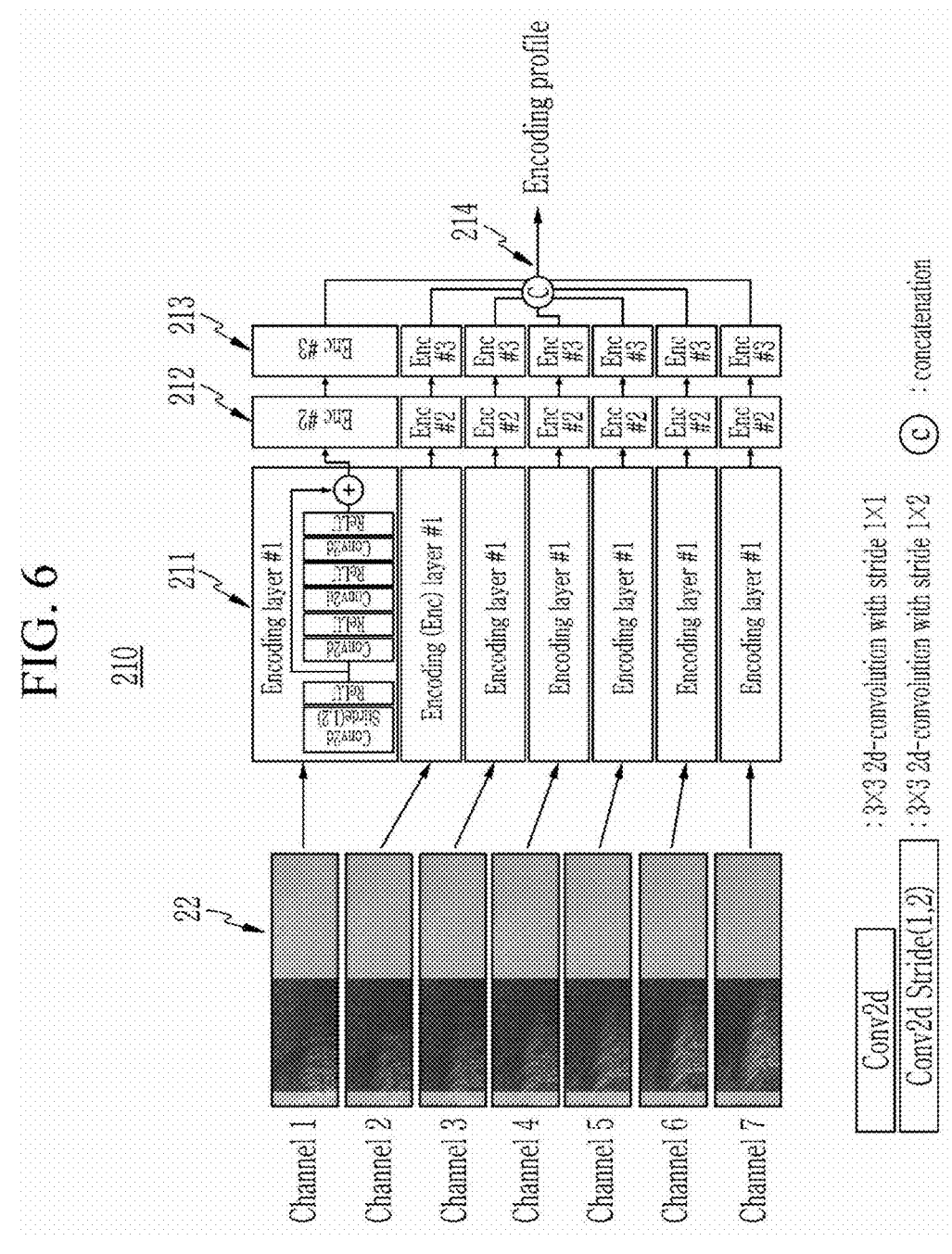
FIG. 6 is a diagram illustrating a network structure of an encoder according to an exemplary embodiment.
Figure 7:
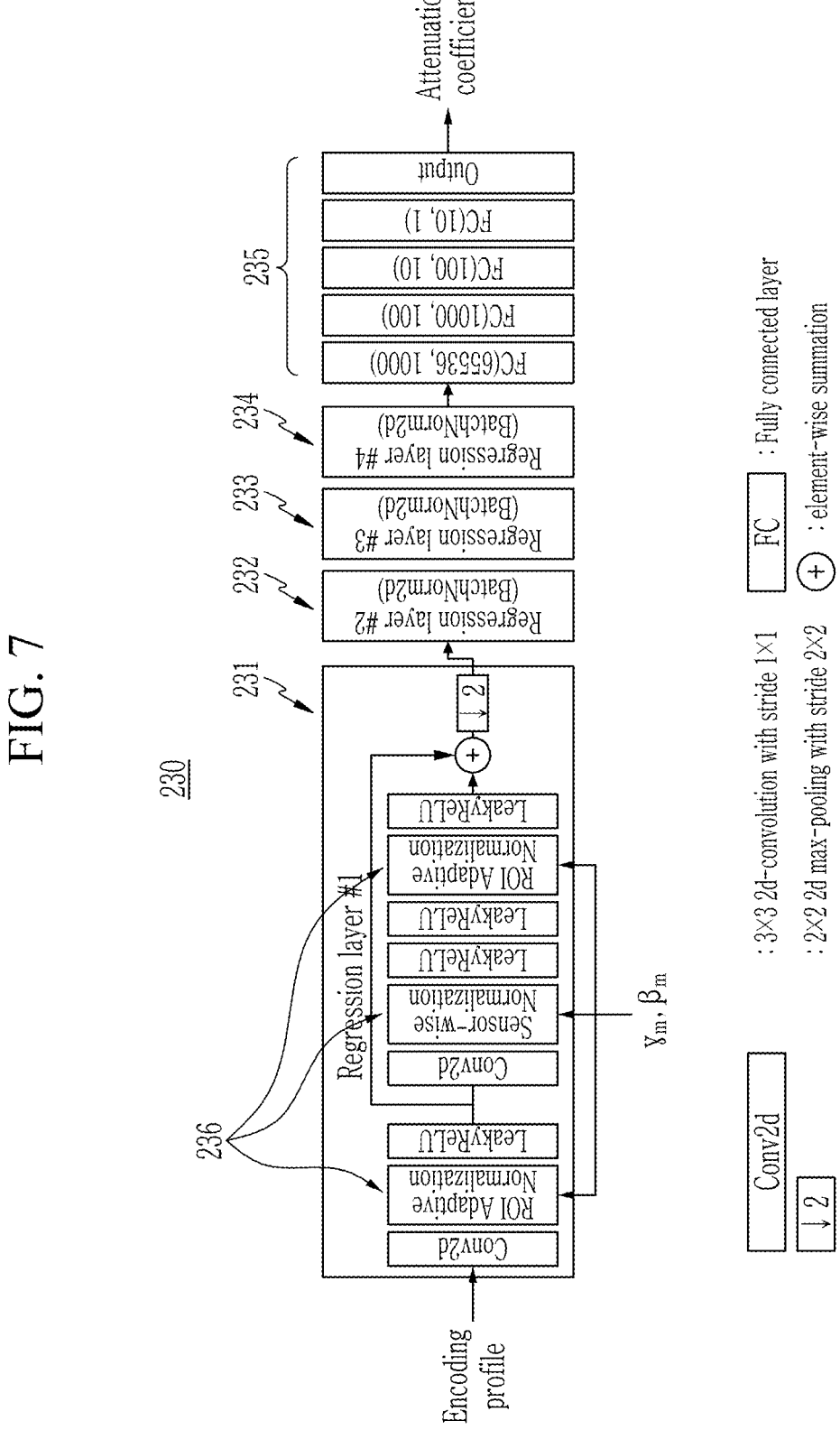
FIG. 7 is a diagram illustrating a structure of a regression network according to an exemplary embodiment.

FIG. 6 is a diagram illustrating a network structure of the encoder according to the exemplary embodiment, and FIG. 7 is a diagram illustrating a structure of the regression network according to the exemplary embodiment.

Referring to FIG. 6, the encoder 210 may encode the input for each channel corresponding to the steering angle of the beam pattern. The encoder 210 may receive input of the pulse-echo data 22 including the ROI data. The encoder 210 may receive images of the envelope detected pulse-echo data cropped to the ROI. Each channel encodes the input through the sequential convolutional-based encoding layers 211, 212, and 213. The output encoded for each channel may be integrated at a node 214, and an encoding profile for the attenuation feature may be output from the node 214.

Each encoding layer may be configured as a residual network. Each encoding path may start with a 3×3 two-dimensional convolutional layer and a ReLU layer on a 1×2 stride.

Referring to FIG. 7, the regression network 230 may extract the attenuation coefficients contained in the encoding profile through the sequential regression layers 231, 232, 233, and 234, and output the attenuation coefficient through a fully connected layer (FC) 235.

At least one of the sequential regression layers 231, 232, 233, and 234 may include an ROI adaptive normalization (RAN) module that adaptively normalizes sensor-specific data based on the location of a region of interest.

For example, the first regression layer 231 may be implemented as a continuous unit blocks with skip connection implemented. A unit block may include, for example, a 3×3 two-dimensional convolutional layer, a normalization layer, and a Leaky ReLU layer. In this case, the normalization layer 236 may be an ROI adaptive normalization (RAN) layer that adaptively normalizes sensor-specific data based on the location of the region of interest. The normalization layer 236 may normalize each sensor's feature x(n, m) to X(n,m) by $\gamma_m$ and $\beta_m$ according to Equation 2.

Since the encoding profile is extracted from the pulse-echo data cropped according to the ROI, the regression network 230 normalizes the features of each sensor according to the location of the ROI. This allows the encoding profile to be adaptively normalized according to the location of the ROI in the sensor dimension.

Subsequently, the regression layers 232, 233, and 234 following the first regression layer 231 may reconstruct the attenuation coefficients from the features while batch normalizing.

Figure 8:
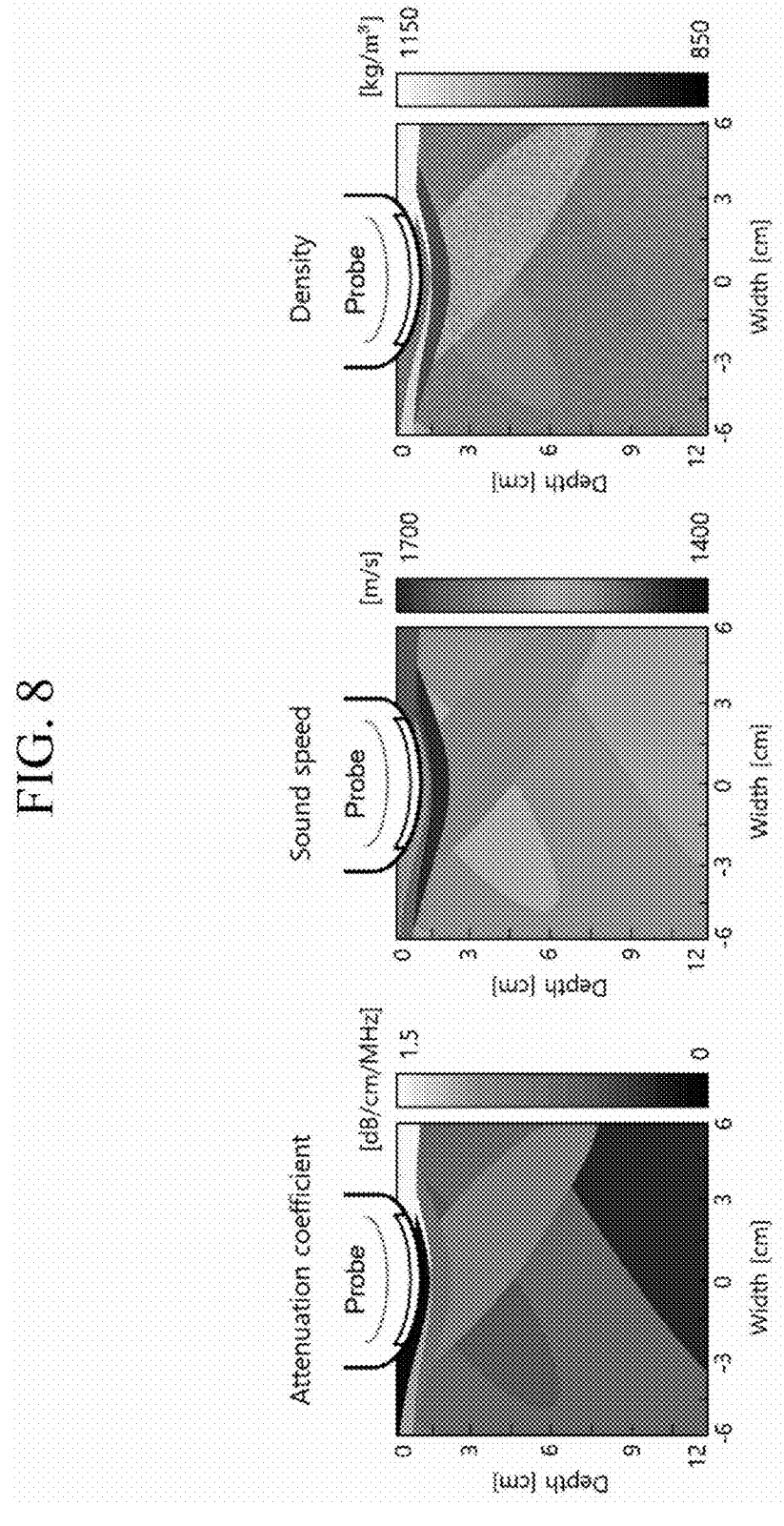
FIG. 8 is a diagram illustrating an example of a simulation phantom.

FIG. 8 is a diagram illustrating an example of a simulation phantom.

Referring to FIG. 8, for training the neural network 200, simulation phantoms may be implemented to represent the area being ultrasonography. For example, for training the neural network 200 to extract quantitative information from an abdominal ultrasound, simulation phantoms that mimic organs and lesions in the abdomen may be created.

For example, in a simulation phantom, one to five ellipses with radii ranging from 10 mm to 100 mm are placed at random locations to represent organs and lesions. In addition, in the simulation phantom, five ellipses with an axial radius of 1 mm to 2 mm and a lateral radius of 10 mm to 100 mm may be placed at a depth of 30 mm to represent subcutaneous fat.

To model the propagation characteristics of the organ, the liver, the sound velocity may be set from 1500 m/s to 1600 m/s, the attenuation coefficient may be set from 0 dB/MHz/cm to 1.5 dB/MHz/cm, and the background density may be set from 900 kg/m$^3$ to 1100 kg/m$^3$. The speed of sound for the ellipse object representing subcutaneous fat may be set from 1400 m/s to 1700 m/s. To model scatterers, no more than 10 scatterers may be evenly distributed over the unit area.

The training data for the neural network 200 may include pulse-echo data obtained from simulation phantoms, and may be collected using an ultrasound simulation tool (e.g., k-wave toolbox of Matlab). For example, the neural network 200 may be trained with 4,000 simulation phantoms. Here, 3200 phantoms may be used for training, 400 phantoms may be used for validation, and 400 phantoms may be used for testing.

The location of the ROI in the simulation phantom may be adjusted between a certain depth range (for example, 40 mm to 90 mm) and a certain steering angle range. The size of the ROI may be set to ±5 mm in the depth axis and ±2° in the angle axis. The pulse-echo data may be cropped to include an additional vertical region of ±35 mm around the region of interest.

A training device may train the neural network 200 to estimate the quantitative information of the simulation phantom, i.e., the attenuation coefficient, using the pulse-echo data obtained via the simulation phantom. For convenience, the quantitative information extraction device 100 is described as training the neural network 200, but the neural network 200 may be trained by a separate device and then installed in the quantitative information extraction device 100.

The objective function J may be defined as shown in Equation 3, and the neural network 200 is trained to minimize a loss between the estimated output and a ground truth.

$$J = \underset{E,P}{\arg\min} E\left[ \|Y - G(E_{1:7}, P)\| + \lambda \sum_i \|w_i\|^2 \right]$$ (Equation 3)

In Equation 3, Y is the ground truth and G(E$_{1:7}$,P) is the output of the neural network 200. E$_{1:7}$ is the input pulse-echo data, which may be pulse-echo data cropped according to the location of the ROI. P is a value representing the ROI location (depth and steering angle), which may be represented as a vector. λ is a normalization parameter, which is used to normalize the weight w$_i$ of the neural network to avoid overfitting.

FIG. 9 is a flowchart of a training method for a neural network according to an exemplary embodiment.

Referring to FIG. 9, the quantitative information extraction device 100 receives the pulse-echo data for training obtained from the simulation phantom and the quantitative information for the ground truth as training data (S110). The quantitative information may be an attenuation coefficient. The location of the ROI in the simulation phantom may be adjusted between a certain depth and a certain steering angle. Pulse-echo data for training may be collected by using ultrasound simulation tools.

The quantitative information extraction device 100 performs a pre-processing to generate ROI pulse-echo data from the pulse-echo data for training based on the location of ROI (S120). The location of the ROI may be represented as a vector representing a depth and a steering angle of the ROI. In some cases, the preprocessing to generate the ROI pulse-echo data may be omitted.

The quantitative information extraction device 100 inputs the pre-processed pulse-echo data and the normalization parameters for each sensor according to the location of ROI into the neural network 200, and trains the neural network 200 to minimize the loss between an estimated output and a ground truth (S130). The neural network 200 may include the encoder 210 to encode quantitative features included in the pulse-echo data, and the regression network 230 to extract quantitative information from the output of the encoder 210. The regression network 230 may include a ROI adaptive normalization layer that normalizes the feature of each sensor by using normalization parameters for each sensor.

Figure 10:
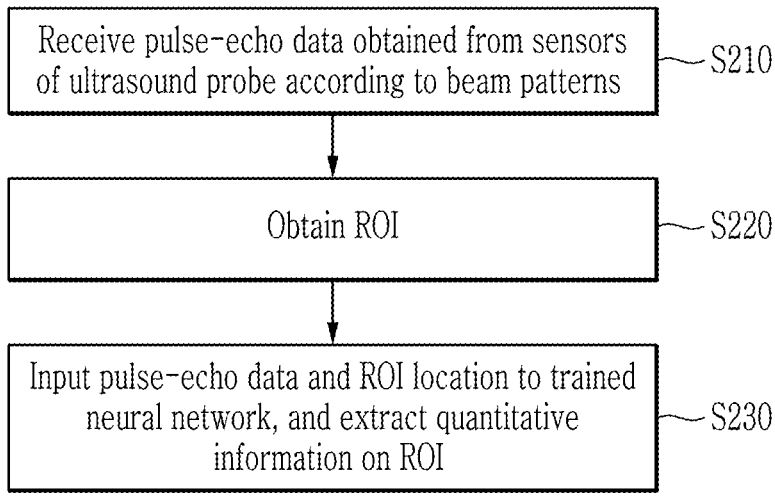
FIG. 10 is a flowchart of a quantitative information extraction method according to an exemplary embodiment.

FIG. 10 is a flowchart of a quantitative information extraction method according to an exemplary embodiment.

Referring to FIG. 10, the quantitative information extraction device 100 receives pulse-echo data obtained from the sensors of the ultrasound probe 10 according to beam patterns (S210). The pulse-echo data is RF data that is reflected back from the tissue by sequentially radiating ultrasound signals in various beam patterns. The beam pattern may be defined by a focal depth and a steering angle.

The quantitative information extraction device 100 obtains a region of interest (ROI) (S220). The quantitative information extraction device 100 may receive the ROI selected from the B-mode image generated from the pulse-echo data. The location of the ROI may be represented as a vector representing a depth and a steering angle of the region of interest.

The quantitative information extraction device 100 inputs the pulse-echo data and the location of the ROI to the trained neural network 200, and extracts the quantitative information on the ROI (S230). The neural network 200 normalizes the feature of each sensor by using normalization parameters for each sensor extracted based on the location of the ROI, and then extract the quantitative information included in the encoding profile. The neural network 200 may be trained to extract the attenuation coefficient of the ROI (e.g., liver region), and may extract the attenuation coefficient used to determine hepatic steatosis.

Meanwhile, the quantitative information extraction device 100 may extract the pulse-echo data of the ROI from the pulse-echo data, based on the location of the ROI, and input the extracted pulse-echo data to the neural network 200. The information extraction device 100 may crop the pulse-echo data of the ROI from the pulse-echo data by using a crop mask generated based on the location of the ROI.

FIG. 11 is a flowchart of a quantitative information providing method based on abdominal ultrasound according to an exemplary embodiment.

Referring to FIG. 11, the quantitative information extraction device 100 receives abdominal pulse-echo data obtained from the sensors of the ultrasound probe 10 according to the beam patterns radiated to the abdomen (S310). The pulse-echo data is RF data that is reflected back from the tissue by sequentially radiating ultrasound signals in various beam patterns. The beam pattern may be defined by a focal depth and a steering angle. The user (operator) may find a liver region while checking a B-mode image of the abdomen using the ultrasound probe 10, and when the B-mode image that appropriately displays the liver region is obtained, the user may press a specific button to acquire data for quantitative analysis. The ultrasound probe 10 then emits beam patterns for quantitative analysis, and pulse-echo data may be acquired.

The quantitative information extraction device 100 provides the B-mode image generated from the abdominal pulse-echo data to an interface screen, and obtains a location of a ROI (S320). The ROI may include a partial region of the liver.

The quantitative information extraction device 100 extracts quantitative information on the ROI, using the abdominal pulse-echo data and the location of the ROI, through the trained neural network 200 (S330). The neural network 200 may normalize the feature of each sensor by using the normalization parameters of each sensor extracted according to the location of the region of interest, and then extract the attenuation coefficients from the encoding profile. The location of the ROI may be represented as a vector representing a depth and a steering angle. The quantitative information extraction device 100 may crop the pulse-echo data of the ROI by using a crop mask generated based on the location of the ROI, and input the cropped pulse-echo data into the neural network 200.

The quantitative information extraction device 100 provides quantitative information including an attenuation coefficient, and analysis extracted based on the quantitative information to the interface screen (S340). The analysis may include information on the liver, for example, a fat percentage related to the hepatic steatosis. Alternatively, the analysis may include information on the presence of hepatic steatosis, or a grade of hepatic steatosis. Based on the relationship between the attenuation coefficient and the fatty liver, the quantitative information extraction device 100 may determine whether the extracted attenuation coefficient corresponds to a normal liver/hepatic steatosis, and determine a hepatic steatosis grade (mild, moderate, and the like) corresponding to the attenuation coefficient.

Figure 13:
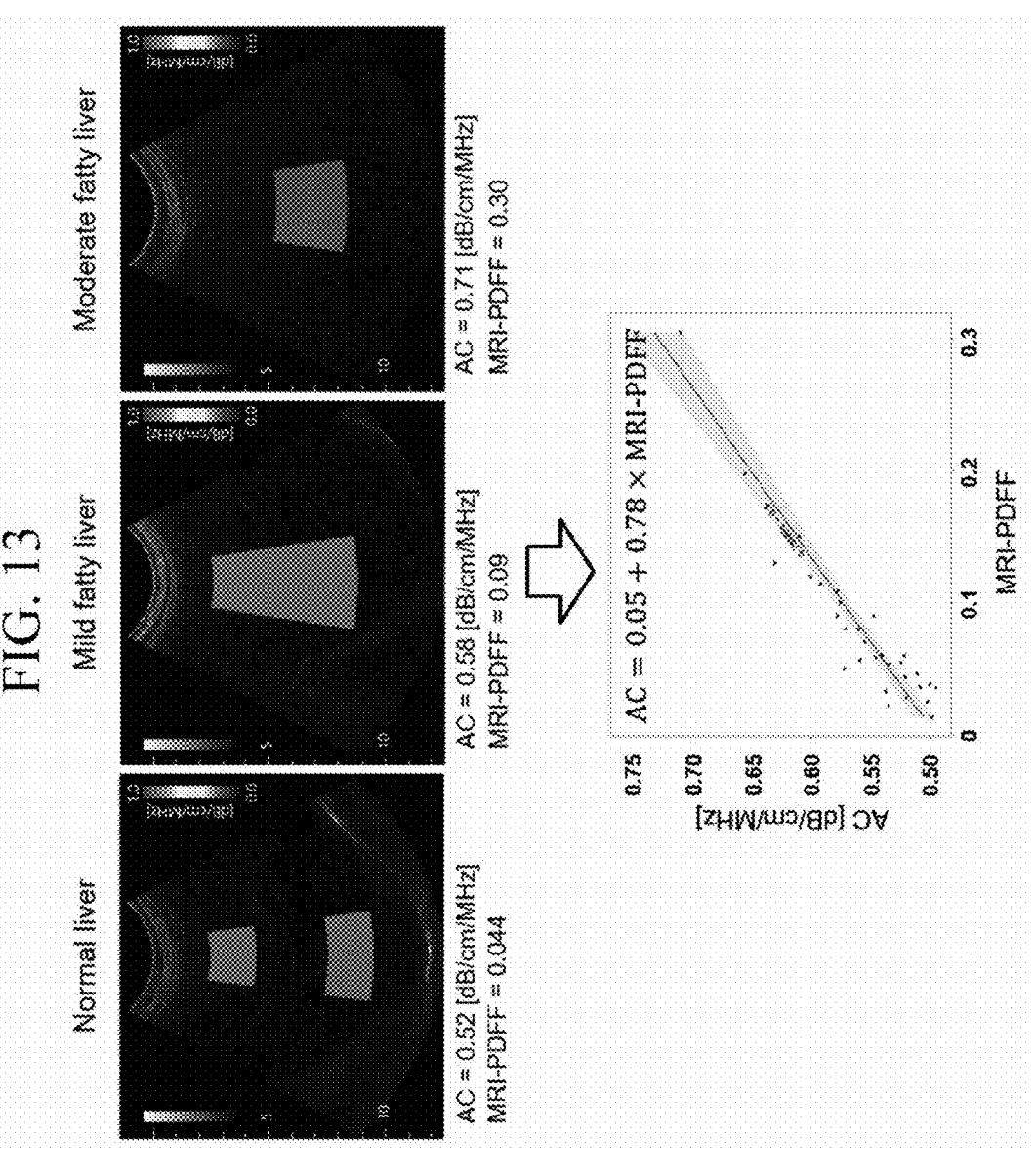

FIGS. 12 and 13 are diagrams illustrating a result of extracting an attenuation coefficient by using the neural network according to an exemplary embodiment.

Referring to FIG. 12, the results of the phantom test using an abdominal phantom show that the neural network 200 performing region-of-interest adaptive normalization may accurately extract the attenuation coefficient of the region of interest compared to other networks.

Referring to FIG. 13, the neural network 200 performing region-of-interest adaptive normalization may extract attenuation coefficients for abdominal ultrasounds of normal liver and hepatic steatosis grades (mild, moderate, and the like). It can be seen that the attenuation coefficients extracted by the neural network 200 are strongly correlated with the MRI-PDFF. MRI-PDFF is the Proton Density Fat Fraction (PDFF) obtained by using Magnetic Resonance Imaging (MRI) for normal liver and hepatic steatosis grades (mild, moderate, and the like).

Figure 14:
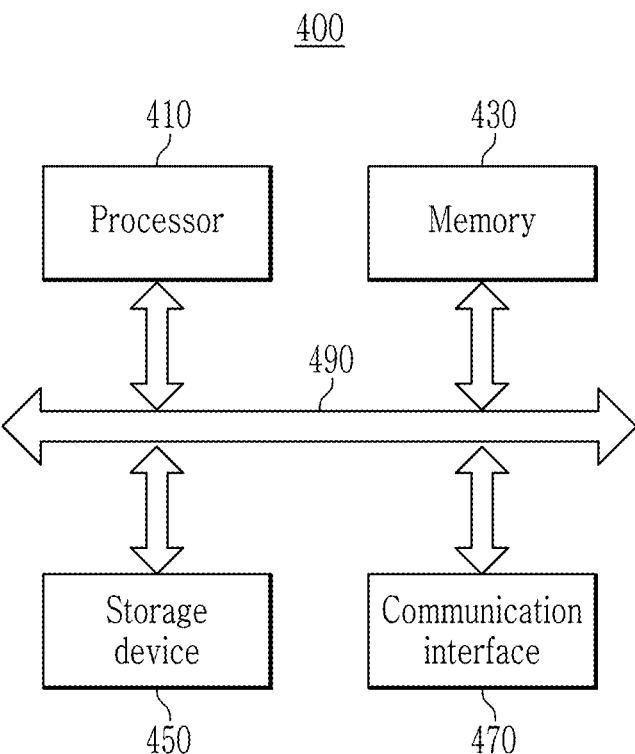
FIG. 14 is a block diagram of a computing device according to an exemplary embodiment.

FIG. 14 is a block diagram of a computing device according to an exemplary embodiment.

Referring to FIG. 14, the quantitative information extraction device 100 may be a computing device 400 operated by at least one processor. The computing device 400 may be associated with the ultrasound probe 10 or a device that provides data acquired by the ultrasound probe 10.

The computing device 400 may include one or more processors 410, a memory 430 for loading programs executed by the processor 410, a storage 450 for storing programs and various data, a communication interface 470, and a bus 490 connecting the processor 410, the memory 430, the storage 450, and the communication interface 470. In addition, the computing device 400 may further include various other components. The program may include instructions that cause the processor 410 to perform the methods/operations according to various exemplary embodiments of the disclosure, when the program is loaded into the memory 430. That is, by executing the instructions, the processor 410 may perform the methods/operations according to various exemplary embodiments of the disclosure. An instruction is a set of computer-readable instructions grouped by function that is a component of a computer program and executed by a processor.

The processor 410 controls the overall operation of each configuration of the computing device 400. The processor 410 may include at least one of a Central Processing Unit (CPU), a Micro Processor Unit (MPU), a Micro Controller Unit (MCU), a Graphics Processing Unit (GPU), or any other form of processor well known in the art of the present disclosure. Further, the processor 410 may perform computations for at least one application or program for executing the methods/operations according to various exemplary embodiments of the present disclosure.

The memory 430 stores various data, instructions, and/or information. The memory 430 may load one or more programs from the storage 450 to execute the methods/operations according to various exemplary embodiments of the present disclosure. The memory 430 may be implemented as volatile memory, such as RAM, but the technical scope of the present disclosure is not limited thereto.

The storage 450 may store programs non-temporarily. The storage 450 may include non-volatile memory, such as a Read Only Memory (ROM), an Erasable Programmable ROM (EPROM), an Electrically Erasable Programmable ROM (EEPROM), a flash memory, or the like, a hard disk, a removable disk, or any other form of computer-readable recording medium well known in the art to which this disclosure belongs.

The communication interface 470 supports wired and wireless communication of the computing device 400. To this end, the communication interface 470 may be configured to include communication modules well known in the art of the present disclosure.

The bus 490 provides a communication function between the components of the computing device 400. The bus 490 may be implemented as various types of buses, such as an address bus, a data bus, and a control bus.

Thus, according to the exemplary embodiment, it is possible to extract quantitative information by using the ultrasound probe and the imaging device for B-brightness mode imaging without change, and in particular, it is possible to obtain the attenuation coefficient that is a biomarker used to determine hepatic steatosis through ultrasound.

According to the exemplary embodiment, it is possible to increase estimation accuracy and noise resilience through the ROI adaptive beam focusing and envelope detection.

According to the exemplary embodiment, it is possible to accurately extract attenuation coefficients through region-of-interest adaptive normalization. According to the exemplary embodiment, it is possible to provide clinical validity through the correlation between the extracted attenuation coefficient and Proton Density Fat Fraction (PDFF) acquired by using MRI.

The exemplary embodiments of the present disclosure described above are not only implemented through the apparatus and method, but may also be implemented through programs that realize functions corresponding to the configurations of the exemplary embodiment of the present disclosure, or through recording media on which the programs are recorded.

Although an exemplary embodiment of the present disclosure has been described in detail, the scope of the present disclosure is not limited by the exemplary embodiment. Various changes and modifications using the basic concept of the present disclosure defined in the accompanying claims by those skilled in the art shall be construed to belong to the scope of the present disclosure.

The invention claimed is:

1. A method for extracting quantitative information by a device operated by at least one processor, the method comprising:

receiving pulse-echo data obtained from sensors of an ultrasound probe according to beam patterns radiated into a tissue;

obtaining a region of interest (ROI); and extracting quantitative information on the ROI from the pulse-echo data by using a neural network trained to extract quantitative information from input data, wherein the neural network normalizes a feature of each sensor by using normalization parameters of each sensor extracted according to a location of the ROI.

2. The method of claim 1, wherein the obtaining the ROI includes obtaining the location of the ROI in a B-mode image generated from the pulse-echo data.

3. The method of claim 1, further comprising:

extracting pulse-echo data of the ROI from the pulse-echo data according to a location of the ROI; and inputting the pulse-echo data of the ROI into the neural network.

4. The method of claim 1, wherein the neural network is configured to encode a quantitative feature included in the input pulse-echo data to generate an encoding profile, and extract quantitative information from the encoding profile while normalizing the feature of each sensor through a ROI adaptive normalization layer.

5. The method of claim 1, wherein the quantitative information is an attenuation coefficient.

6. The method of claim 5, wherein the pulse-echo data is abdominal ultrasound data, and the ROI includes a partial region of a liver.

7. The method of claim 6, further comprising:

extracting information on hepatic steatosis in the ROI based on the attenuation coefficient extracted from the pulse-echo data.

8. A method for extracting quantitative information by a device operated by at least one processor, the method comprising:

receiving pulse-echo data obtained from sensors of an ultrasound probe according to beam patterns radiated to an abdomen;

providing a B-mode image generated from the pulse-echo data to an interface screen, and obtaining a region of interest (ROI) from the interface screen;

inputting the pulse-echo data and a location of the ROI to a neural network trained to extract quantitative information from input data, and extracting quantitative information on the ROI; and providing the quantitative information and/or analysis extracted based on the quantitative information to the interface screen, wherein the neural network includes an ROI adaptive normalization layer that normalizes a feature of each sensor by using normalization parameters of each sensor extracted based on the location of ROI.

9. The method of claim 8, further comprising:

extracting information on hepatic steatosis in the ROI based on the quantitative information including an attenuation coefficient.

10. The method of claim 8, wherein the location of the ROI is represented as a vector representing a depth and a steering angle from the ultrasound probe.

11. The method of claim 8, wherein the neural network is configured to encode a quantitative feature included in the input pulse-echo data to generate n encoding profile, and extract an attenuation coefficient of the interest region from the encoding profile while normalizing the feature of each sensor through the ROI adaptive normalization layer.

12. A method for extracting quantitative information by a device operated by at least one processor, the method comprising:

extracting pulse-echo data of a region of interest (ROI) from pulse-echo data obtained according to beam patterns from sensors of an ultrasound probe; and by using a neural network:

encoding the pulse-echo data of the ROI for each channel corresponding to a steering angle of a beam pattern, and integrating outputs encoded for each channel to generate an encoding profile;

normalizing a feature of each sensor included in the encoding profile by using normalization parameters of each sensor extracted based on a location of the ROI; and extracting quantitative information on the ROI from a feature normalized adaptively to the location of the ROI.

13. The method of claim 12, wherein the normalization parameters of each sensor are parameters that scale and shift a feature of each sensor.

14. The method of claim 12, wherein the location of the ROI is represented as a vector representing a depth and a steering angle from the ultrasound probe.

15. The method of claim 12, wherein the extracting the quantitative information on the ROI includes extracting the quantitative information on the ROI by using a regression network trained to extract quantitative information included in the encoding profile through a sequential regression layer.

16. The method of claim 12, wherein the quantitative information is an attenuation coefficient.

17. The method of claim 16, wherein the pulse-echo data is abdominal ultrasound data, and the ROI includes a partial region of a liver.

18. The method of claim 17, further comprising:

extracting information on hepatic steatosis in the region of interest based on the attenuation coefficient of the region of interest.

* * * * *